US00PP23874P2

(12) United States Plant Patent
Smith

(10) Patent No.: US PP23,874 P2
(45) Date of Patent: Sep. 3, 2013

(54) ***CHRYSANTHEMUM* PLANT NAMED 'CIFZ0029'**

(50) Latin Name: *Chrysanthemum×morifolium*
Varietal Denomination: CIFZ0029

(75) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 71 days.

(21) Appl. No.: 13/385,242

(22) Filed: Feb. 9, 2012

(51) Int. Cl.
*A01H 5/00* (2006.01)

(52) U.S. Cl.
USPC ..... Plt./289

(58) Field of Classification Search
USPC ..... Plt./289
See application file for complete search history.

*Primary Examiner* — Annette Para
(74) *Attorney, Agent, or Firm* — Joshua L. Price

(57) ABSTRACT

A new *Chrysanthemum* plant named 'CIFZ0029' particularly distinguished by the medium sized, white decorative inflorescences, medium yellow-green foliage color, rounded plant habit, and a natural season flowering response of mid-September.

1 Drawing Sheet

Latin name of the genus and species of the plant claimed: *Chrysanthemum×morifolium.*

Varietal denomination: 'CIFZ0029'.

BACKGROUND OF THE NEW PLANT

The present invention comprises a new *Chrysanthemum*, botanically known as *Chrysanthemum×morifolium*, and hereinafter referred to by the variety name 'CIFZ0029'.

'CIFZ0029' is a product of a planned breeding program. The new cultivar has medium sized, white decorative inflorescences, medium yellow-green foliage color, rounded plant habit and a natural season flowering response of mid-September.

'CIFZ0029' originated from a hybridization made in November 2007 in a greenhouse in Amanecer, Columbia. The female parent was the unpatented, proprietary plant designated '05-M263', with a smaller inflorescence with yellow ray florets, smaller plant habit and a natural season flowering response that is two weeks earlier than that of 'CIFZ0029'.

The male parent of 'CIFZ0029' was a commercial variety 'Jason', U.S. Plant Pat. No. 14,609, with larger inflorescences, more disc florets, and a rounder and shorter habit than that of 'CIFZ0029'. The resultant seed was sown and grown outdoors in June 2008 in Alva, Fla. USA.

'CIFZ0029' was selected as one flowering plant within the progeny of the stated cross in October 2008 in Alva, Fla.

The first act of asexual reproduction of 'CIFZ0029' was accomplished when vegetative cuttings were propagated from the initial selection in December 2008 in Alva, Fla.

BRIEF SUMMARY OF INVENTION

Horticultural examination of plants grown from cuttings of the plant initiated in December 2008, and continuing thereafter, has demonstrated that the combination of characteristics as herein disclosed for 'CIFZ0029' are firmly fixed and are retained through successive generations of asexual reproduction.

'CIFZ0029' has not been observed under all possible environmental conditions. The phenotype may vary significantly with variations in environment such as temperature, light intensity, and day length.

A Plant Breeder's Right for this cultivar was applied for in Canada on Feb. 24, 2011, No. 11-7186. 'CIFZ0029' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIFZ0029' with colors being as true as possible with an illustration of this type. The photographic drawing shows a flowering potted plant of the new variety and a close-up of the inflorescences.

DETAILED BOTANICAL DESCRIPTION

The plant descriptions, measurements and aforementioned photographs were taken outdoors in Gilroy, Calif. in early August 2011. The plants were growing in an outdoor potted plant trial in one gallon pots in full sun. These plants were approximately 9-10 weeks of age.

Color references are made to The Royal Horticultural Society Colour Chart (R.H.S.) 2001.

TABLE 1

DIFFERENCES BETWEEN THE NEW VARIETY 'CIFZ0029' AND A MOST SIMILAR VARIETY

| | 'CIFZ0029' | 'Yohelga' (U.S. Plant Pat. No. 13,811) |
|---|---|---|
| Immature ray floret color: | More yellow | Lighter yellow/closer to white |

TABLE 1-continued

DIFFERENCES BETWEEN THE NEW VARIETY 'CIFZ0029' AND A MOST SIMILAR VARIETY

| | 'CIFZ0029' | 'Yohelga' (U.S. Plant Pat. No. 13,811) |
|---|---|---|
| Black cloth flowering response: | 10 days faster | 10 days slower |
| Plant habit in wet weather: | Less apt to split apart | More apt to split apart |

Plant:

*Form, growth and habit.*—Herbaceous garden-type, stems upright and outwardly spreading, freely branching, moderately vigorous growth habit.

*Plant height.*—17.0-18.0 cm.

*Plant height (inflorescence included).*—21.0-23.0 cm.

*Plant width.*—38.0-41.0 cm.

Roots:

*Number of days to initiate roots.*—About 4 days at about 22 degrees C.

*Number of days to produce a rooted cutting.*—4-6 days at 22 degrees C.

*Type.*—Fine, fibrous, free branching.

*Color.*—RHS N155B but whiter.

Foliage:

*Arrangement.*—Alternate.

*Immature, leaf color, upper surface.*—Closest to RHS 147A but more green.

*Lower surface.*—Closest to RHS 147B.

*Mature, leaf color, upper surface.*—Closest to RHS 147A but more green.

*Lower surface.*—Closest to RHS 147B.

*Length.*—5.2-5.4 cm.

*Width.*—4.2-5.0 cm.

*Shape.*—Ovate.

*Base shape.*—Attenuate.

*Apex shape.*—Mucronulate.

*Margin.*—Palmately lobed; irregularly incised; serrate.

*Texture, upper surface.*—Bifid T-shaped hairs.

*Lower surface.*—Bifid T-shaped hairs.

*Color of veins, upper surface.*—Closest to RHS 147A becoming indistinct.

*Color of veins, lower surface.*—Indisinct from foliage color.

*Petiole color.*—Closest to RHS 147B but a little greener.

*Length.*—2.5-2.8 cm.

*Diameter.*—0.2-0.25 cm.

*Texture.*—Bifid T-shaped hairs.

Stem:

*Quantity of main branches per plant.*—7-8.

*Color of stem.*—Closest to RHS 146A.

*Length of stem.*—11.0-15.0 cm.

*Diameter.*—0.4-0.45 cm.

*Length of internodes.*—1.5-2.0 cm.

*Texture.*—Bifid T-shaped hairs.

*Color of peduncle.*—Closest to RHS 146A.

*Length of peduncle.*—8.5-11.0 cm.

*Peduncle diameter.*—0.2 cm.

*Texture.*—Bifid T-shaped hairs.

Inflorescence:

*Type.*—Compositae, solitary decorative-type inflorescences, borne terminally above foliage, ray florets arranged acropetally on a capitulum.

*Quantity of inflorescences per plant.*—About 125, with 50-75 buds.

*Lastingness of individual blooms on the plant.*—About 6 weeks from first color showing.

*Fragrance.*—Slightly spicy.

Bud (just when opening/showing color):

*Color.*—RHS 8B.

*Length.*—0.7-1.3 cm.

*Width.*—1.0-1.2 cm.

*Shape.*—Oblate.

Immature inflorescence:

*Diameter.*—About 4.0 cm.

*Color of ray florets, upper surface.*—RHS 4C to RHS 4D.

*Lower surface.*—RHS 4D.

Mature inflorescence:

*Diameter.*—6.0-7.0 cm when fully flattened out.

*Depth.*—2.5-3.0 cm in natural form.

*Total diameter of disc.*—0.2 cm, found only in very mature inflorescences.

*Receptacle height.*—0.3-0.4 cm.

*Receptacle diameter.*—0.4 cm.

Ray florets:

*Average quantity of florets.*—About 130 in several whorls.

*Color of florets, upper surface.*—RHS 155D but more white.

*Lower surface.*—RHS 155D but more white.

*Length.*—3.2-3.6 cm.

*Width.*—0.5-0.6 cm.

*Shape.*—Narrowly obovate.

*Apex shape.*—Obtuse to some retuse or emarginate.

*Margin.*—Entire.

*Texture, upper surface.*—Papillose.

*Lower surface.*—Papillose.

Disc florets:

*Average quantity of florets.*—50-60.

*Color of florets.*—RHS 14B.

*Length.*—0.4-0.5 cm.

*Width.*—0.1 cm.

*Shape.*—Tubular, elongated.

*Apex shape.*—Acute, 5 pointed.

Phyllaries:

*Quantity.*—20-30.

*Color, upper surface.*—Between RHS 147A and RHS 147B.

*Lower surface.*—RHS 147B, appears lighter due to hairs.

*Length.*—Average 0.7-0.8 cm, a few are actually closer to 1.0 cm.

*Width.*—0.2 cm.

*Shape.*—Lanceolate.

*Apex shape.*—Acute.

*Base.*—Fused.

*Margins.*—Entire.

*Texture, upper surface.*—Glabrous.

*Lower surface.*—Bifid T-shaped hairs.

Reproductive organs:

*Pistil.*—1, found on both types of florets.

*Length.*—Those in ray florets are 0.6 cm; those in the disc florets are 0.3 cm.

*Style color.*—RHS 1C.

*Style length.*—0.5 cm.

*Stigma color.*—RHS 14B.

*Stigma shape.*—Bi-parted; frilly.

*Ovary color.*—RHS 155C and very translucent looking.

*Ovary length.*—0.05 cm.

*Ovary width*.—0.05 cm.
*Stamens*.—4, found on only on the disc florets.
*Color of filaments*.—RHS 1C.
*Length filaments*.—0.3-0.4 cm.
*Anther color*.—RHS 13B.
*Anther length*.—0.15 cm.
*Anther shape*.—Oblong.
*Color of pollen*.—RHS 14A.
*Pollen amount*.—Scarce.

What is claimed is:

1. A new and distinct variety of *Chrysanthemum* plant named 'CIFZ0029' substantially as illustrated and described herein.

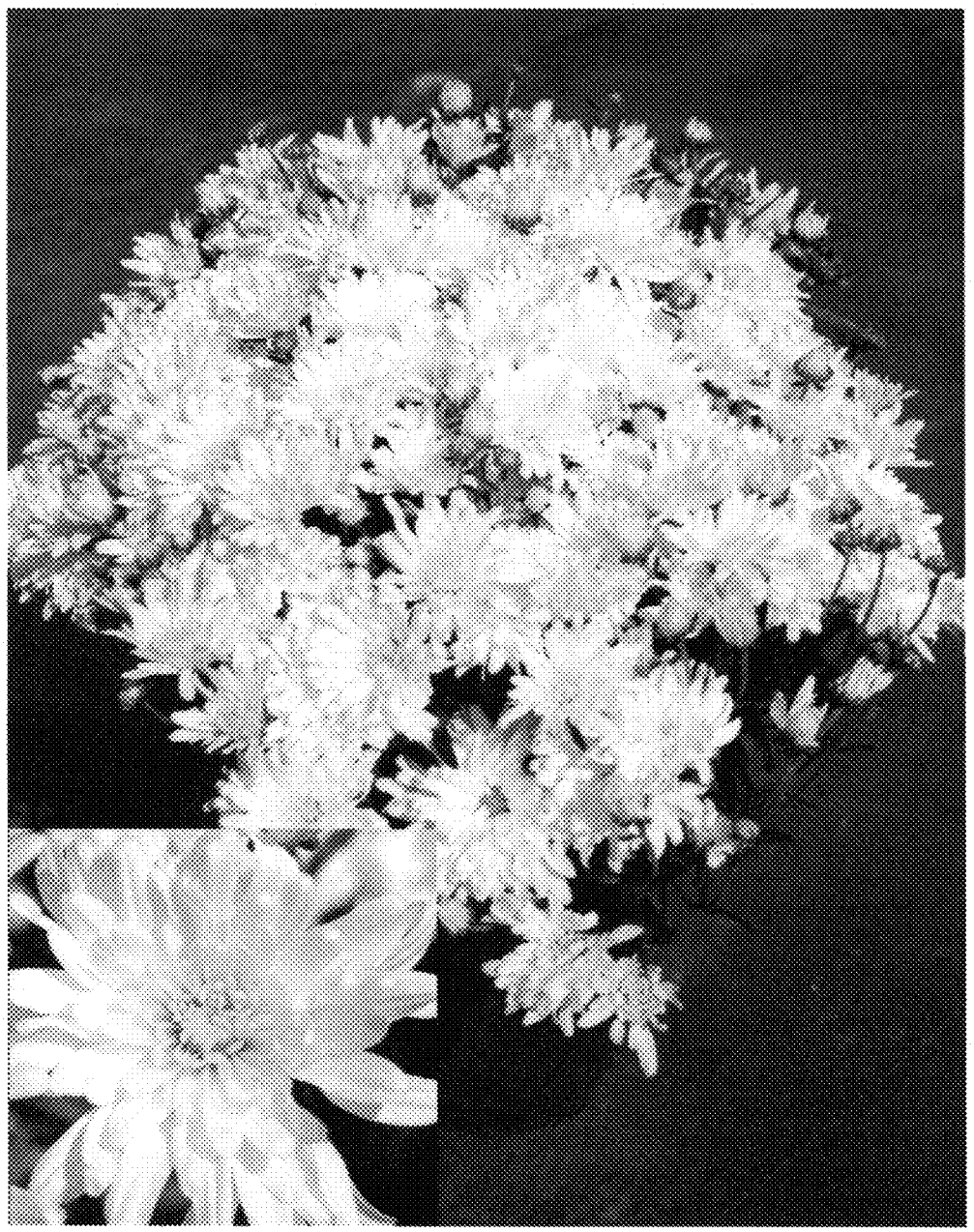

* * * * *